(12) United States Patent
Hardy et al.

(10) Patent No.: US 11,390,847 B2
(45) Date of Patent: Jul. 19, 2022

(54) ELECTROACTIVE POLYMERIC SCAFFOLDS AND METHOD FOR DELIVERING NERVE GROWTH FACTOR TO NERVE TISSUE

(71) Applicant: University of Florida Research Foundation, Inc., Gainesville, FL (US)

(72) Inventors: John Hardy, Little Common Bexhill-on-Sea (GB); Christine E. Schmidt, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/788,851

(22) Filed: Feb. 12, 2020

(65) Prior Publication Data

US 2020/0181570 A1    Jun. 11, 2020

Related U.S. Application Data

(62) Division of application No. 14/491,686, filed on Sep. 19, 2014, now Pat. No. 10,597,636.

(51) Int. Cl.

| | | |
|---|---|---|
| *C12N 5/079* | (2010.01) | |
| *C12N 5/0793* | (2010.01) | |
| *C12N 5/00* | (2006.01) | |
| *C12N 5/077* | (2010.01) | |

(52) U.S. Cl.
CPC ......... *C12N 5/0622* (2013.01); *C12N 5/0068* (2013.01); *C12N 5/0618* (2013.01); *C12N 5/0619* (2013.01); *C12N 5/0656* (2013.01); *C12N 2501/13* (2013.01); *C12N 2533/30* (2013.01); *C12N 2533/40* (2013.01); *C12N 2539/00* (2013.01)

(58) Field of Classification Search
CPC .. C12N 5/0622; C12N 5/0068; C12N 5/0618; C12N 2533/40; C12N 2529/00
See application file for complete search history.

(56) References Cited

U.S. PATENT DOCUMENTS

| | | | |
|---|---|---|---|
| 6,095,148 | A | 8/2000 | Shastri |
| 6,569,654 | B2 | 5/2003 | Shastri et al. |
| 6,696,575 | B2 | 2/2004 | Schmidt |
| 8,563,626 | B2 | 10/2013 | Olayo Gonzalez et al. |
| 2010/0087885 | A1* | 4/2010 | Atanasoska ............ A61N 1/378 607/9 |
| 2013/0105167 | A1* | 5/2013 | Norman .................. C04B 28/02 166/308.1 |
| 2013/0195955 | A1 | 8/2013 | Reichert et al. |
| 2013/0331869 | A1 | 12/2013 | Runge |
| 2014/0099277 | A1* | 4/2014 | Adhikari ............ A61L 27/3817 525/450 |

FOREIGN PATENT DOCUMENTS

| | | |
|---|---|---|
| WO | 9310806 | 6/1993 |
| WO | 2009094225 | 7/2009 |
| WO | 2009130515 | 10/2009 |
| WO | 2011004971 | 1/2011 |
| WO | 2013154780 | 10/2013 |

OTHER PUBLICATIONS

Aziz "Li+ ion conduction mechanism in poly (e-caprolactone)-based polymer electrolyte" iran polym J 22:877-883 (Year: 2013).*
Lubasova "Cell Growth on Porous and Non-Porous Polycaprolactone Nanofibers" nanocon (Year: 2010).*
Ravichandran "Applications of conducting polymers and their issues in biomedical engineering" j r soc interface 7:s559-s579 (Year: 2010).*
International Search Report and the Written Opinion of the International Searching Authority Issued in PCT/US2015/050594 dated Feb. 2, 15 pages.
Xianchun Chen, et al., Preparation of Carboxylic Graphene Oxide-composited Polypyrrole Conduits and their Effect on Sciatic Nerve Repair under Electrical Stimulation, Journal of Biomedical Materials Research Part A, Aug. 13, 2019.
Hong-Chang Tian, et al., Enhanced Flexible Tubular Microelectrode with Conducting Polymer for Multi-Functional Implantable Tissue-Machine Interface, Scientific Reports 6, Article No. 26910 (2016).
Thitima Sudwilai, et al., Polypyrrole-coated electrospun poly (lactic acid) fibrous scaffold: effects of coating on electrical conductivity and neural cell growth, Journal of Biomaterials Science, Polymer Edition, pp. 1240-1252, Jun. 16, 2014.
Chengyun Ninga, et al., Electroactive polymers for tissue regeneration: Developments and perspectives, Prog Polym Sci Jun. 2018; 81:144-162. doi:10.1016/j.progpolymsci.2018.01.001.
Bo Zhu, et al., Large enhancement in neurite outgrowth on a cell membrane-mimicking conducting polymer, Nature Communications, Nature Communications 5, Article No. 4523 (2014).
Juan Wang, et al., In vitro and in vivo studies of electroactive reduced graphene oxide-modified nanofiber scaffolds for peripheral nerve regeneration, Acta Biomaterialia, vol. 84, Jan. 15, 2019, pp. 98-113.
Chengyun Ning, et al., Electroactive polymers for tissue regeneration: Developments and perspectives, Prog Polym Sci. Jun. 2018; 81:144-162. Published online May 7, 2018. doi: 10.1016/j.progpolymsci.2018.01 .001.

(Continued)

*Primary Examiner* — Adam Weidner
(74) *Attorney, Agent, or Firm* — Thomas | Horstemeyer, LLP

(57) ABSTRACT

A polymerizable unit that yields an electrochemically responsive polymer (advantageously pyrrole) is anchored by polymerization within a polycaprolactone matrix to form an electroactive scaffold upon which cells can be cultured and in which the micro- and nano-topological features of the polycaprolactone matrix are preserved. A scaffold manufactured in accordance with the preferred embodiment can support Schwann cells, which produce nerve growth factor when electrically stimulated. Nerve growth factor has been demonstrated to promote the regeneration of nerve tissue. By implanting the scaffold on which Schwann cells have been cultured into damaged nerve tissue and applying a voltage across the scaffold, nerve growth factor is produced, thereby promoting repair of the damaged nerve tissue.

20 Claims, 1 Drawing Sheet

(56) References Cited

OTHER PUBLICATIONS

Zhuqun Shi, et al., In Situ Synthesis of Robust Conductive Cellulose/Polypyrrole Composite Aerogels and Their Potential Application in Nerve Regeneration, Angewandte Chemie International Edition, Apr. 7, 2014.

Rajiv Borah, et al., Electrically conductive MEH-PPV:PCL electrospun nanofibres for electrical stimulation of rat PC12 pheochromocytoma cells, Biomaterials Science, Issue 9, 2018.

Ann M. Rajnicek, et al., Controlling Nerve Growth with an Electric Field Induced Indirectly in Transparent Conductive Substrate Materials, Advanced Healthcare Materials, 2018, 7, 1800473.

Luigi Aloe, et al. Nerve growth factor: from the early discoveries to the potential clinical use, Journal of Translational Medicine, vol. 10: 239, 2012, 15 pages.

Mark H. Tuszynski, et al. Aphase 1 clinical trial of nerve growth factor gene therapy for Alzheimer disease, Nature Medicine, vol. 11, No. 5, May 2005, pp. 551-555.

Eric C. Spivey, et al. The fundamental role of subcellular topography in peripheral nerve repair therapies, Biomaterials, vol. 22, 2012, pp. 4264-4276.

M. Brett Runge, et al. Development of Electrically Conductive Oligo(polyehtylene glycol) Fumarate-Polypyrrole Hydrogels for Nerve Regeneration, Biomacromolecules, vol. 11, 2010, pp. 2845-2853.

Philipp Moroder, et al. Material properties and electrical stimulation regimens of polycaprolactone fumarate-polypyrrole scaffolds as potential conductive nerve conduits, Acta Biomaterialia, vol. 7, 2011, pp. 944-953.

M. Brett Runge, et al. The development of electrically conductive polycaprolactone fumarate-polypyrrole composite materials for nerve regeneration, Biomaterials, vol. 31, 2010, pp. 5916-5926.

\* cited by examiner

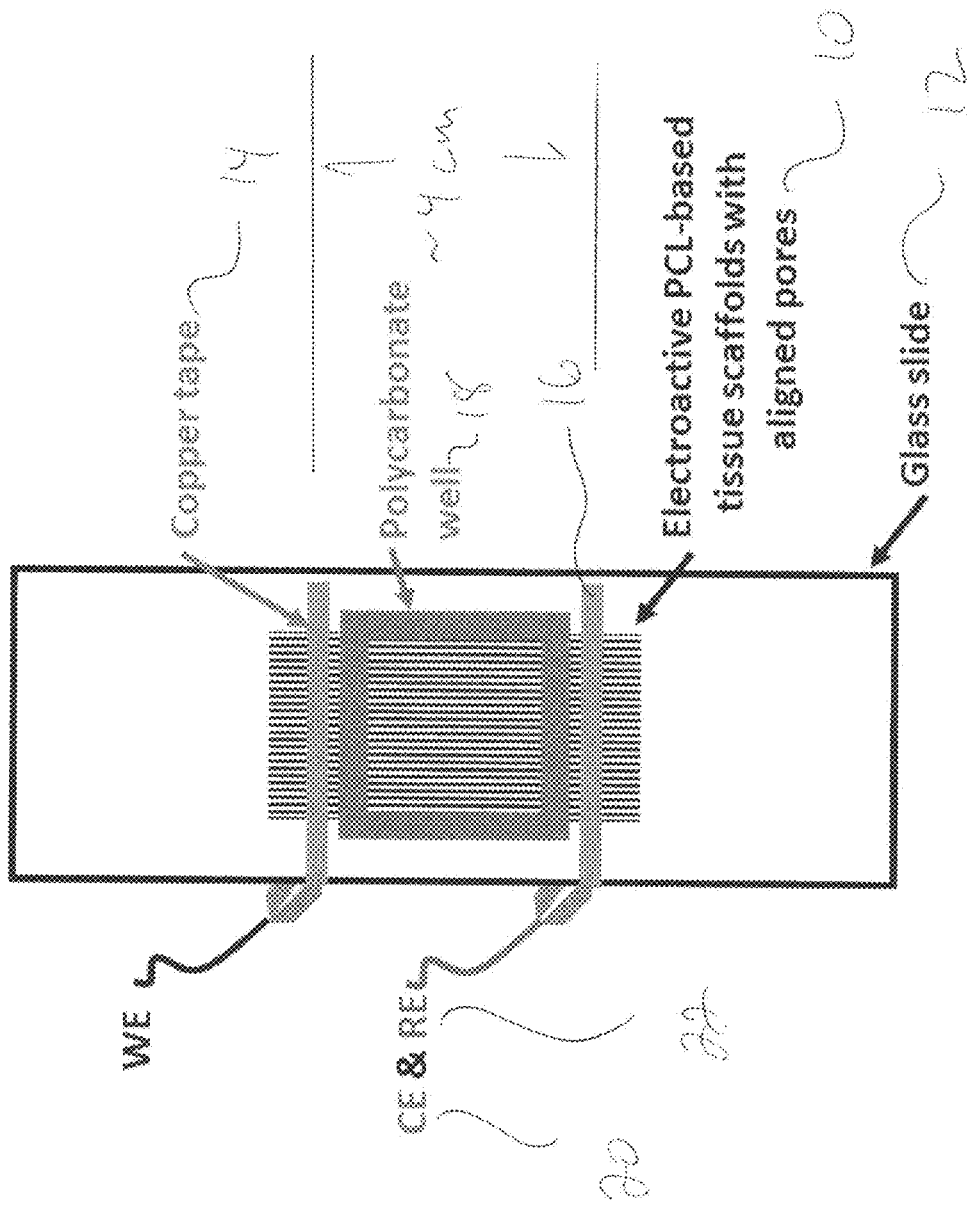

ELECTROACTIVE POLYMERIC SCAFFOLDS AND METHOD FOR DELIVERING NERVE GROWTH FACTOR TO NERVE TISSUE

CROSS-REFERENCE TO RELATED APPLICATIONS

This application is a divisional of U.S. application Ser. No. 14/491,686, entitled "ELECTROACTIVE POLYMERIC SCAFFOLDS AND METHOD FOR DELIVERING NERVE GROWTH FACTOR TO NERVE TISSUE" filed on Sep. 19, 2014, of which is hereby incorporated by reference in its entirety.

BACKGROUND OF THE INVENTION

The invention relates to biomaterials, and more particularly relates to electroactive biomaterials. In its most immediate sense, the invention relates to delivery of nerve growth factor to nerve tissue, and to implantable electroactive scaffolds used for such delivery.

When a peripheral nerve has a defect of more than two centimeters, a biomaterial is needed to repair the defect. This is conventionally done using either an autologous nerve graft (i.e. by taking a functioning section of a nerve from elsewhere in the patient's body) or using an allograft (i.e. by using a section of a nerve that has been removed from another living individual or from a cadaver). An autologous graft causes a loss of function from the site where the nerve section was removed, and an allograft is expensive. It would therefore be advantageous to provide a biomaterial having properties similar to an autologous nerve graft or a nerve allograft, so that the biomaterial could be used to repair peripheral nerve defects.

The invention proceeds from the realization that when a polymerizable electrically responsive unit such as pyrrole is anchored by polymerization within a polycaprolactone matrix in order to form an electroactive scaffold upon which cells can be cultured, the micro- and nano-topological features of the polycaprolactone matrix can be preserved. And, when pyrrole is so anchored within a polycaprolactone matrix, Schwann cells can be cultured on the scaffold. Schwann cells are known to increase the production of nerve growth factor when electrically stimulated, and nerve growth factor has been demonstrated to promote regeneration of nerve tissue. Hence, in accordance with the invention, nerve growth factor can be delivered to nerve tissue by implanting in the tissue a scaffold in accordance with the invention upon which Schwann cells have been cultured, and electrically stimulating the Schwann cells.

However, use of pyrrole is not essential to the practice of the invention. Another polymerizable unit can be used instead of pyrrole, provided the product is electrochemically responsive.

While the invention is motivated by the need to deliver nerve growth factor to repair nerve tissue, it can have other applications. Scaffolds in accordance with the invention can be used to deliver drugs, antibacterial agents, and antifungal agents. They can also be used as electroactive actuators capable of mechanotransduction of stem cells.

BRIEF DESCRIPTION OF THE DRAWINGS

The invention will be better understood with reference to the following illustrative and non-limiting drawing, in which:

FIG. 1 shows the experimental setup used to electrically stimulate rat Schwann cells which increases the production of nerve growth factor by the Schwann cells.

DETAILED DESCRIPTION OF PREFERRED EMBODIMENTS

1. Production of Electroactive Polycaprolactone-Based Scaffolds

Initially, pyrrole was purified by passage over basic alumina. A polycaprolactone matrix with aligned pores was placed in a solution of the pyrrole (291 µL, [84 mM], 1 eq.) and polystyrenesulfonate (0.799 g, [84 mM], 1 eq., Mn 70 kDa) in a solvent of distilled water (50 mL). Samples were sonicated for five minutes and cooled to 4° C. for one hour. Thereafter, ferric chloride (1.848 g, [228 mM], 2.7 eq.) was added as an initiator, the mixture was shaken to assure dissolution of the ferric chloride, and the shaken mixture was then incubated for a further twenty four hours at 4° C. Electroactive scaffolds with an interpenetrating network of polypyrrole and polystyrenesulfonate) were removed from the reaction mixture, placed in fresh distilled water, sonicated for five minutes, and then exhaustively washed (to remove monomers, oligomers and initiators) with deionized water until the water was clear, colorless and the pH was neutral (approximately forty-eight hours). The scaffolds were then dried under high vacuum at 21° C.

Electroactive polycaprolactone-based scaffolds so prepared have their microscale and nanoscale topological properties preserved. This is advantageous because clinical evidence suggests that micro- and nano-topographical features incorporated into scaffolds is beneficial for the restoration of nerve tissue.

2. Preparation and Sterilization of Electroactive-Coated Polycaprolactone-Based Scaffolds The dried scaffolds with aligned pores were incubated in an aqueous solution of poly-D-lysine (PDL, 50 µg/mL) for one hour and then washed thoroughly with sterile water to remove any weakly adsorbed poly-D-lysine (exchanging the water every ten minutes for one hour). Samples were inserted in untreated polystyrene tissue culture plates and sterilized by incubation in 70% ethanol solution, followed by exposure to UV for sixty minutes.

3. In Vitro Culture of Human Dermal Fibroblasts

Growth medium for human dermal fibroblasts was composed of: high glucose Dulbecco's Modified Eagle Medium (DMEM, 440 mL); fetal bovine serum (50 mL); antibiotic-antimycotic (5 mL); non-essential amino acids (5 mL), and 2 ng/mL basic fibroblast growth factor. The sterilized scaffolds were incubated for thirty minutes under three millimeters of this growth medium. The growth medium was aspirated and replaced before seeding with human dermal fibroblasts at 5,000 cells/cm$^2$ under three millimeters of medium, and incubated at 37° C., 95% humidity, and a $CO_2$ content of 5%. Cell viability before starting the experiment was determined by the Trypan Blue (Sigma, USA) exclusion method, and the measured viability exceeded 95% in all cases. After two days the medium was aspirated, the scaffolds were washed gently with phosphate-buffered saline, the cells were fixed with 4% paraformaldehyde in phosphate-buffered saline for fifteen minutes, and the scaffolds were washed again with phosphate-buffered saline (3×1 mL).

The human dermal fibroblasts were observed to adhere to the scaffolds.

4. In Vitro Culture of Schwann Cells

Schwann cell growth medium was composed of: 25.5 mL of low glucose Dulbecco's Modified Eagle Medium (DMEM); 8.5 mL of GIBCO® Ham's F-12 Nutrient Mixture; 350 µL Penicillin Streptomycin (1% of the final volume); 350 µL N2 supplement (2% of the final volume); Forskolin [5 µM]; and Neuregulin-1β (50 ng/mL). The sterilized scaffolds were incubated for thirty minutes under three millimeters of this growth medium. The growth medium was aspirated and replaced before seeding with rat Schwann cells at 5,000 cells/cm$^2$ under three millimeters of medium, and incubated at 37° C., 95% humidity, and a $CO_2$ content of 5%. Cell viability before starting the experiment was determined by the Trypan Blue (Sigma, USA) exclusion method, and the measured viability exceeded 95% in all cases. After two days the medium was aspirated, the scaffolds were washed gently with phosphate-buffered saline, the cells were fixed with 4% paraformaldehyde in phosphate-buffered saline for fifteen minutes, and the scaffolds were washed again with phosphate-buffered saline (3×1 mL).

The Schwann cells were observed to adhere to the scaffolds.

5. Electrical Stimulation of Schwann Cells

Non-conductive glass slides, polycarbonate wells (2.5 cm square polycarbonate blocks 1 cm thick, sides of 2.5 cm, with 0.9 cm square holes cut out of them), Dow Corning® high vacuum grease, and medium binder clips were sterilized by autoclave. Polystyrene petri dishes (diameter of 10 cm) had holes drilled in their sides and were sterilized by exposure to ultraviolet radiation for sixty minutes. Adhesive-backed copper tape (5 mm width, Ted Pella, Inc.), waterproof Kapton® tape (1 cm width, Fisher Scientific, Waltham, Mass.), wires and alligator clips were sterilized by exposure to ultraviolet radiation for sixty minutes.

Electroactive polycaprolactone-based sterilized scaffolds with aligned pores 10 were placed on sterilized glass slides 12 and secured in position with two thin strips 14, 16 of sterilized adhesive-backed copper tape that were attached to the scaffolds 10, parallel to one another, separated by a distance of approximately four centimeters. A polycarbonate well 18 for holding the Schwann cell growth medium was mounted watertight to the slide 12. The counter and reference electrodes (20 and 22 respectively) were connected together to the strip 16, and the working electrode 24 was clipped to the strip 14. Schwann cells were plated and cultured as described above. A potential step of +50 mV/mm was placed across the substrate for the duration of 1 hour, after which the wires were disconnected and the substrates cultured as normal.

The amount of nerve growth factor expressed by rat Schwann cells under electrical stimulation was measured and compared with the amount of nerve growth factor expressed by rat Schwann cells that were not electrically stimulated and that served as controls. The electrically stimulated cells in the electroactive PCL-based tissue scaffolds with aligned pores 10 were exposed to a potential difference of 50 mV/mm.

The concentration of NGF in the medium (in pg/mL) was determined (using a Rat NGF ELISA Kit, Insight Genomics, Falls Church, Va.) immediately after electrical stimulation and thereafter in intervals of twelve hours for three days. There were no significant differences in NGF production by Schwann cells in any of the non-stimulated controls over the three day study, whereas, after forty eight hours in culture the rat Schwann cells responded to the electrical stimulation by increased production of NGF, a trend that was markedly more apparent during the following twenty four hours to approximately three times the amount produced by an equivalent number of rat Schwann cells cultured without electrical stimulation. Such increases in nerve growth factor production have been shown to encourage neurite outgrowth from neurons in a number of studies.

6. In-Vitro Degradation of Electroactive Polycaprolactone-Based Scaffolds

To demonstrate that enzymatic/hydrolytic degradation of the electroactive polycaprolactone-based scaffolds is possible, the scaffolds were incubated in phosphate-buffered saline in the absence or presence of a high concentration (4 units/mL) of cholesterol esterase, an enzyme known to hydrolyze ester bonds in polyesters. When incubated in phosphate-buffered saline for twelve days the mass of the scaffolds did not change significantly because hydrolysis of phosphate-buffered saline occurs very slowly. The presence of the esterase increased the rate of hydrolysis, resulting in an approximately 50% mass loss over 12 days. The presence of the electroactive polyelectrolyte complex of polypyrrole and polystyrenesulfonate appears to increase the hydrophilicity of the scaffolds allowing the enzyme to more easily access the polycaprolactone chains. The scaffolds are likely to degrade slowly if administered in vivo (over the period of several months) in line with other polycaprolone-based materials, leaving behind the residual water insoluble polyelectrolyte complex of polypyrrole and polystyrenesulfonate that preclinical trials have shown to be relatively non-immunogenic. Indeed, histological analyses of tissue in the vicinity of polypyrrole-based tissue scaffolds implanted subcutaneously or intramuscularly in rats, showed immune cell infiltration comparable to FDA-approved poly(lactic acid-co-glycolic acid) [Schmidt C E, Shastri V R, Vacanti J P, Langer R: Stimulation of neurite outgrowth using an electrically conducting polymer. Proc Natl Acad Sci USA 1997, 94:8948-8953] or poly(D,L-lactide-co-glycolide). Wang Z, Roberge C, Dao L H, Wan Y, Shi G, Rouabhia M, Guidoin R, Zhang Z: In vivo evaluation of a novel electrically conductive polypyrrole/poly(D,L-lactide) composite and polypyrrole-coated poly(D,L-lactide-co-glycolide) membranes. J Biomed Mater Res A 2004, 70:28-38 Similarly, there was no significant inflammation in the vicinity of polypyrrole-based materials implanted in the coronary artery of rats after 5 weeks, [Mihardja S S, Sievers R E, Lee R L: The effect of polypyrrole on arteriogenesis in an acute rat infarct model. Biomaterials 2008, 29:4205-4210] sciatic nerve guidance channels implanted in rats after 8 weeks, [Durgam H, Sapp S, Deister C, Khaing Z, Chang E, Luebben S, Schmidt C E: Novel degradable co-polymers of polypyrrole support cell proliferation and enhance neurite outgrowth with electrical stimulation. J Biomater Sci Polym Ed 2010, 21: 1265-1282] or electrodes in rat brains after 3 or 6 weeks. [George P M, Lyckman A W, LaVan D A, Hegde A, Leung Y, Avasare R, Testa C, Alexander P M, Langer R, Sur M: Fabrication and biocompatibility of polypyrrole implants suitable for neural prosthetics. Biomaterials 2005, 26:3511-3519

7. Alternates to Pyrrole

As stated above, use of pyrrole is not essential to practicing the invention. Another polymerizable unit yielding an electrochemically-responsive polymer can be used instead of pyrrole. Examples of such polymerizable units yielding electrochemically-responsive polymers are: an aniline, an aniline derivative, a furan, a furan derivative, a thiophene, a thiophene derivative, a ferrocene, a ferrocene derivative, a porphyrin; and a porphyrin derivative.

Use of ferric chloride as an initiator is not necessary to practice the invention. Other initiators, such as ammonium persulfate and peroxides can be used instead. So, too, water need not be used as the solvent; other solvents can also be suitable as long as the polycaprolactone is insoluble in them. Quite obviously, the initiator and solvent to be used will be determined by the choice of polymerizable electrochemical unit.

8. Nerve Tissue Therapy

As stated above, Schwann cells are known to produce nerve growth factor when electrically stimulated. In accordance with the invention, Schwann cells are cultured on the above-described scaffolds and the scaffolds with the Schwann cells cultured on them are implanted into the peripheral nerve tissue to be repaired. Delivery of nerve growth factor to the nerve tissue is accomplished by applying a voltage across the scaffolds and thereby electrically stimulating the Schwann cells. The nerve growth factor thereby produced promotes regeneration of nerve tissue.

Although a preferred embodiment has been described above, the scope of the invention is limited only by the following claims:

The invention claimed is:

1. An electroactive tissue scaffold, comprising:
   a. a polycaprolactone matrix; and
   b. a polymerizable unit yielding an electrochemically responsive polymer located in the pores of the matrix and anchored thereto by polymerization.

2. The scaffold of claim 1, wherein the scaffold is biodegradable.

3. The scaffold of claim 1, wherein the polymerizable unit yielding an electrochemically responsive polymer is an aromatic compound.

4. The scaffold of claim 3, wherein the aromatic compound is heterocyclic.

5. The scaffold of claim 4, wherein the heterocyclic aromatic compound is a pyrrole.

6. The scaffold of claim 1, wherein the polymerizable unit yielding an electrochemically responsive polymer is selected from a group consisting of:
   a. an aniline;
   b. an aniline derivative;
   c. a furan;
   d. a furan derivative;
   e. a thiophene;
   f. a thiophene derivative;
   g. ferrocene;
   h. a ferrocene derivative;
   i. a porphyrin; and
   j. a porphyrin derivative.

7. The scaffold of claim 6, wherein 1 the polymerizable unit yielding an electrochemically responsive polymer is selected from a group consisting of:
   a. 3,4-ethylenedioxythiophene; and
   b. a derivative of 3,4-ethylenedioxythiophene.

8. The scaffold of claim 1, wherein the scaffold is bioerodible.

9. The electroactive tissue scaffold of claim 1, wherein the electroactive tissue scaffold further comprises Schwann cells.

10. An electroactive tissue scaffold produced by a process comprising:
    a. obtaining polycaprolactone;
    b. obtaining a polymerizable unit that yields an electrochemically responsive polymer; and
    c. polymerizing the electrochemically responsive unit and the polycaprolactone in a solvent, the solvent being chosen such that the polycaprolactone is insoluble therein.

11. The electroactive tissue scaffold produced by the process of claim 10, further comprising culturing Schwann cells on the tissue scaffold after the polymerizing.

12. A method of manufacturing an electroactive tissue scaffold, comprising the following steps:
    a. obtaining polycaprolactone;
    b. obtaining a polymerizable unit that yields an electrochemically responsive polymer; and
    c. initiating a polymerization of the polycaprolactone and the electrochemically responsive unit with an initiator in the presence of a solvent in which the polycaprolactone is insoluble.

13. The method of claim 12, wherein the solvent is water and the polymerizable unit that yields an electrochemically responsive polymer is chosen such that the scaffold is bioerodible.

14. The method of claim 13, wherein the polymerizable unit that yields an electrochemically responsive polymer is an aromatic compound.

15. The method of claim 14, wherein the aromatic compound is heterocyclic.

16. The method of claim 15, wherein the polymerizable unit that yields an electrochemically responsive polymer is a pyrrole derivative.

17. The method of claim 12, wherein the polymerizable unit that yields an electrochemically responsive polymer is pyrrole, the solvent is water, and the initiating step is carried out using polystyrenesulfonate and the initiator ferric chloride.

18. The method of claim 17, further comprising the step of washing the scaffold.

19. A method of manufacturing a polycaprolactone-based electroactive tissue scaffold, comprising the following steps:
    a. obtaining a polycaprolactone matrix;
    b. obtaining pyrrole;
    c. polymerizing the pyrrole in an aqueous solution that includes the polycaprolactone matrix, polystyrenesulfonate and ferric chloride to produce a polycaprolactone-based electroactive scaffold; and
    d. washing the polycaprolactone-based electroactive scaffold to remove the ferric chloride and unbound polystyrenesulfonate.

20. The method of claim 19, further comprising culturing Schwann cells on the tissue scaffold after the washing.

* * * * *